(12) United States Patent
Suzuki

(10) Patent No.: US 11,229,423 B2
(45) Date of Patent: Jan. 25, 2022

(54) TISSUE COLLECTING INSTRUMENT

(71) Applicant: nano grains Co., Ltd., Nagano (JP)

(72) Inventor: Keita Suzuki, Nagano (JP)

(73) Assignee: NANO GRAINS CO., LTD., Nagano (JP)

( * ) Notice: Subject to any disclaimer, the term of this patent is extended or adjusted under 35 U.S.C. 154(b) by 708 days.

(21) Appl. No.: 15/496,373

(22) Filed: Apr. 25, 2017

(65) Prior Publication Data

US 2017/0311936 A1 Nov. 2, 2017

(51) Int. Cl.
*A61B 10/02* (2006.01)
*A61B 17/34* (2006.01)

(52) U.S. Cl.
CPC ...... *A61B 10/0275* (2013.01); *A61B 17/3421* (2013.01)

(58) Field of Classification Search
CPC ............ A61B 10/0275; A61B 17/3421; A61B 10/0266; A61B 10/0233
See application file for complete search history.

(56) References Cited

U.S. PATENT DOCUMENTS

| | | | |
|---|---|---|---|
| 5,320,110 A | | 6/1994 | Wang |
| 5,458,112 A | | 10/1995 | Weaver |
| 5,507,742 A | * | 4/1996 | Long .................. A61B 17/3417 606/15 |
| D657,461 S | * | 4/2012 | Schembre .......... A61B 10/0275 D24/130 |
| 9,844,362 B2 | * | 12/2017 | McWeeney .......... A61B 8/0841 |
| 10,034,684 B2 | * | 7/2018 | Weisenburgh, II ......................... A61B 18/1206 |
| 2002/0022788 A1 | | 2/2002 | Corvi et al. |
| 2005/0070818 A1 | | 3/2005 | Mueller, Jr. |

(Continued)

FOREIGN PATENT DOCUMENTS

| | | | |
|---|---|---|---|
| EP | 0019104 A2 | * 11/1980 | ......... A61B 10/0275 |
| JP | 10-137248 | 5/1998 | |

(Continued)

OTHER PUBLICATIONS

Japanese Office Action for JP Application No. 2016-089749 dated Feb. 6, 2020.

(Continued)

*Primary Examiner* — Jacqueline Cheng
*Assistant Examiner* — Tho Q Tran
(74) *Attorney, Agent, or Firm* — Kowert, Hood, Munyon, Rankin & Goetzel, P.C.; Gareth M. Sampson

(57) ABSTRACT

A tissue collecting instrument which cuts and collects tissue includes a first member formed in a tubular shape and including an internal space and a side hole communicating with the internal space, a second member inserted into the internal space and configured to be movable relative to the first member, a first protruding portion provided on the first member and configured to protrude toward the inside of the side hole, and a second protruding portion provided on the second member and configured to protrude in a direction opposite to the first protruding portion, wherein the tissue is able to enter the internal space through the side hole when the first member and the second member are in a positional relationship in which the first protruding portion and the second protruding portion are spaced apart and facing each other.

2 Claims, 8 Drawing Sheets

(56) References Cited

U.S. PATENT DOCUMENTS

| | | | |
|---|---|---|---|
| 2007/0106176 A1* | 5/2007 | Mark | A61B 10/0275 |
| | | | 600/566 |
| 2010/0145225 A1* | 6/2010 | Desilets | A61B 17/320783 |
| | | | 600/570 |
| 2013/0046316 A1 | 2/2013 | Sullivan et al. | |
| 2014/0100448 A1 | 4/2014 | Neilan | |
| 2018/0228476 A1* | 8/2018 | Cannon | A61B 10/0275 |
| 2020/0205794 A1* | 7/2020 | Bladen | A61B 10/0233 |

FOREIGN PATENT DOCUMENTS

| | | |
|---|---|---|
| JP | 2006-095312 | 4/2006 |
| JP | 2012-509096 | 4/2012 |
| JP | 2013-523333 | 6/2013 |
| JP | 2013-538615 | 10/2013 |
| JP | B-5450359 | 3/2014 |

OTHER PUBLICATIONS

Japanese Office Action issued for JP 2016-089749 dated Jul. 13, 2020.

\* cited by examiner

TISSUE COLLECTING INSTRUMENT

PRIORITY CLAIM

This application claims priority to Japanese Patent Application No. 2016-089749, filed on Apr. 27, 2016, the content of which is incorporated herein by reference.

BACKGROUND OF THE INVENTION

Field of the Invention

The present invention relates to a tissue collecting instrument inserted into a body.

Description of Related Art

Conventionally, medical instruments have been introduced into a body and various tissues have been collected. As one of medical instruments used for collecting tissues, a biopsy needle which is endoscopically introduced into the body is known.

A distal portion of a typical biopsy needle has a cylindrical shape with a sharp tip. When tissue is pierced by such a biopsy needle, a portion of the tissue is cut into a substantially columnar shape and enters inside of the biopsy needle. However, the portion which has entered the biopsy needle is not easy to be collected because they are still connected to other portion of the tissue in front of the biopsy needle.

In connection with this problem, a biopsy device described in Japanese Patent No. 5450359 has been proposed. This biopsy device includes an inner needle having a notch portion on an outer circumferential surface on a distal side and a hollow outer needle into which the inner needle is inserted, and it is possible to collect tissues into the notch portion while the inner needle and the outer needle are moving forward and backward relative to each other.

In the biopsy device described in Japanese Patent No. 5450359, some of the tissues having entered the notch portion are cut off from other parts of the tissues when the outer needle moves forward relative to the inner needle. However, there is a possibility that some of the tissues that have entered the notch portion may be extruded to the outside of the inner needle when the outer needle relatively moves forward. As a result, it is not always possible to collect a sufficient amount of tissues and the manipulating technique becomes complicated.

SUMMARY OF THE INVENTION

According to a first aspect of the present invention, a tissue collecting instrument which cuts and collects tissue includes a first member formed in a tubular shape and including an internal space and a side hole communicating with the internal space, a second member inserted into the internal space and configured to be movable relative to the first member, a first protruding portion provided on the first member and configured to protrude toward the inside of the side hole, and a second protruding portion provided on the second member and configured to protrude in a direction opposite to the first protruding portion. The tissue is able to enter the internal space through the side hole when the first member and the second member are in a positional relationship in which the first protruding portion and the second protruding portion are spaced apart and facing each other.

The second member may be configured to shield the side hole by being moved relative to the first member.

The tissue collecting instrument may further include a piercing portion provided at a distal portion of the first member or the second member with which the tissue is pierced.

The piercing portion may include a plurality of inclined surfaces inclined with respect to an axis of the first member; and a ridgeline positioned between the plurality of inclined surfaces. The ridgeline may be positioned at a different phase from the first protruding portion in a direction around the axis of the first member.

A cutaway surface of the first member forming a peripheral edge of the side hole may include a first blade surface and a second blade surface adjacent to each other with the first protruding portion interposed therebetween. An edge of the first blade surface and the second blade surface may be formed to be continuous to a tip of the first protruding portion.

A cutaway surface forming a peripheral edge of the side hole may include a first blade surface and a second blade surface which are configured to form the first protruding portion, a first edge surface and a second edge surface which are configured to form an edge portion in a radial direction of the side hole, and a first end surface and a second end surface which are configured to form an edge portion opposite to the first protruding portion in the side hole. The first blade surface, the first edge surface, and the first end surface may be formed to have a common parallel axis.

The second blade surface, the second edge surface, and the second end surface may be formed to have another common parallel axis.

DETAILED DESCRIPTION OF THE INVENTION

Figure 1:
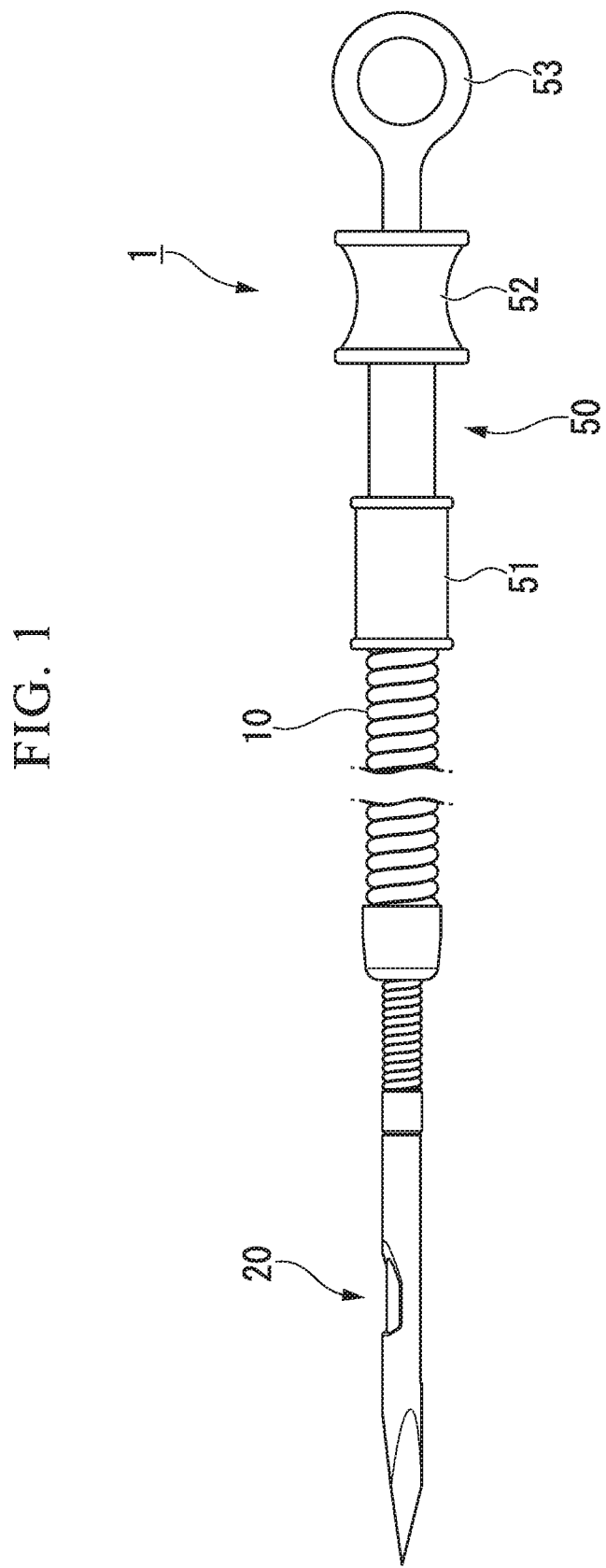
FIG. 1 is a general view of a tissue collecting instrument according to a first embodiment of the present invention.

A tissue collecting instrument according to a first embodiment of the present invention will be described with reference to FIGS. 1 to 12. As illustrated in FIG. 1, a tissue collecting instrument 1 according to the present embodiment includes a long insertion portion 10, a tissue collecting portion 20 inserted into the insertion portion 10, and a manipulator 50 provided at a proximal side of the insertion portion 10 and the tissue collecting portion 20.

The insertion portion 10 is formed in a tubular shape and has flexibility. As illustrated in FIG. 1, the insertion portion 10 of the present embodiment is formed of a known coil sheath, but it may be formed of other materials. The dimensions of the insertion portion 10 such as a length, an outer diameter, and the like can be appropriately set. For example, they may be set to dimensions such that the insertion portion 10 can be inserted into a treatment instrument channel of an endoscope and be made to protrude from and be retracted into a distal opening of the treatment instrument channel.

Figure 2:
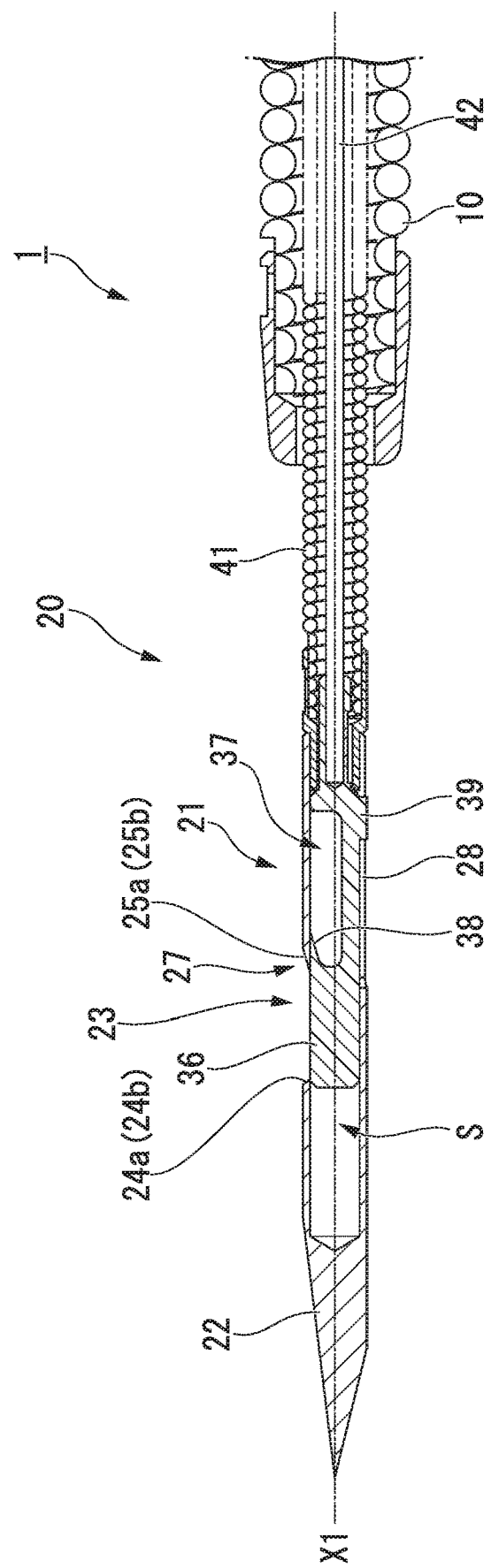
FIG. 2 is an enlarged cross-sectional view of a distal portion of the tissue collecting instrument.

FIG. 2 is an enlarged cross-sectional view illustrating a distal portion of the tissue collecting instrument 1. As illustrated in FIG. 2, a first member 21 inserted into the insertion portion 10 and a second member 36 inserted into the first member 21 are provided in the tissue collecting portion 20.

The first member 21 is formed of a metal or the like in substantially a tubular shape and has a piercing portion 22 which is sharply formed at the distal end portion. In the first member 21 of the present embodiment, the piercing portion 22 has a solid form and a region on the proximal end side from the piercing portion 22 is formed in a tubular shape having an internal space S.

Figure 3:
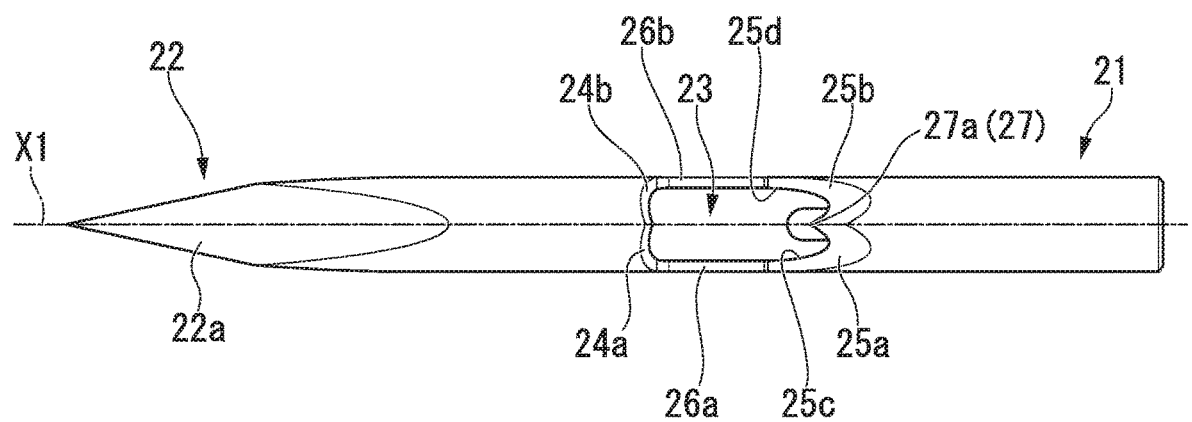
FIG. 3 is a view illustrating a first member of the tissue collecting instrument.

FIG. 3 is an external view of a distal portion of the first member 21. A part of the outer circumferential surface of the tubular portion near the piercing portion 22 is removed in the first member 21. Thereby, a side hole 23 communicating with the internal space S is formed at the distal portion of the region formed in a tubular shape in the first member 21.

Since a part of the outer circumferential surface is removed, a cutaway surface of the first member 21 is formed on a peripheral edge of the side hole 23. The cutaway surface of the first member 21 has six surfaces in total including a first end surface 24a and a second end surface 24b which are formed on the distal side, a first blade surface 25a and a second blade surface 25b which are formed on the proximal end side, a first edge surface 26a positioned between the first end surface 24a and the first blade surface 25a, and a second edge surface 26b positioned between the second end surface 24b and the second blade surface 25b. The first end surface 24a, the first edge surface 26a, and the first blade surface 25a, and the second end surface 24b, the second edge surface 26b, and the second blade surface 25b, are formed to be symmetrical with respect to the central line of an axis X1 of the first member 21.

All of the aforementioned six surfaces are formed to be flat, but angles formed by the surfaces with respect to the axis X1 are different. The first edge surface 26a and the second edge surface 26b are formed parallel to the axis X1. As illustrated in FIG. 2, the first end surface 24a and the second end surface 24b as well as the first blade surface 25a and the second blade surface 25b are inclined to form angles with respect to the axis X1. The angle formed by the first blade surface 25a and the second blade surface 25b with respect to the axis X1 is smaller than the angle formed by the first end surface 24a and the second end surface 24b with respect to the axis X1. Thus, edge portions near the side hole 23 in the first blade surface 25a and the second blade surface 25b are sharp edges 25c and 25d (see FIG. 3).

As illustrated in FIG. 3, the edges 25c and 25d are formed on a curved shape protruding toward the proximal end side of the first member 21. Thereby, a first protruding portion 27 protruding toward the inside of the side hole 23 is formed at a portion adjacent to the first blade surface 25a and the second blade surface 25b. That is, the first blade surface 25a and the second blade surface 25b are positioned on both sides of the first protruding portion 27, and the edges 25c and 25d of the first blade surface 25a and the second blade surface 25b are continuous to a tip 27a of the first protruding portion 27.

Figure 4:
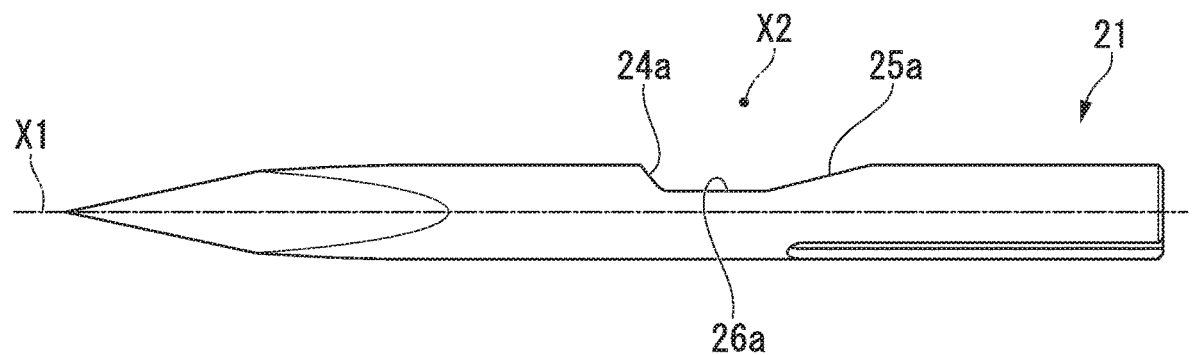
FIG. 4 is a view of the first member viewed from a different direction.

As illustrated in FIG. 4, while the first end surface 24a, the first edge surface 26a, and the first blade surface 25a which are positioned on the same side with respect to the axis X1 have different angles from each other with respect to the axis X1, they have a common parallel axis X2 extending in a direction perpendicular to the axis X1. Therefore, the three flat surfaces of the first end surface 24a, the first edge surface 26a, and the first blade surface 25a can be formed by a single cutting process by moving a laser, a cutter, or the like extending parallel to the parallel axis X2 without changing the extending direction to cut a part off the outer circumferential surface of the first member 21.

Figure 5:
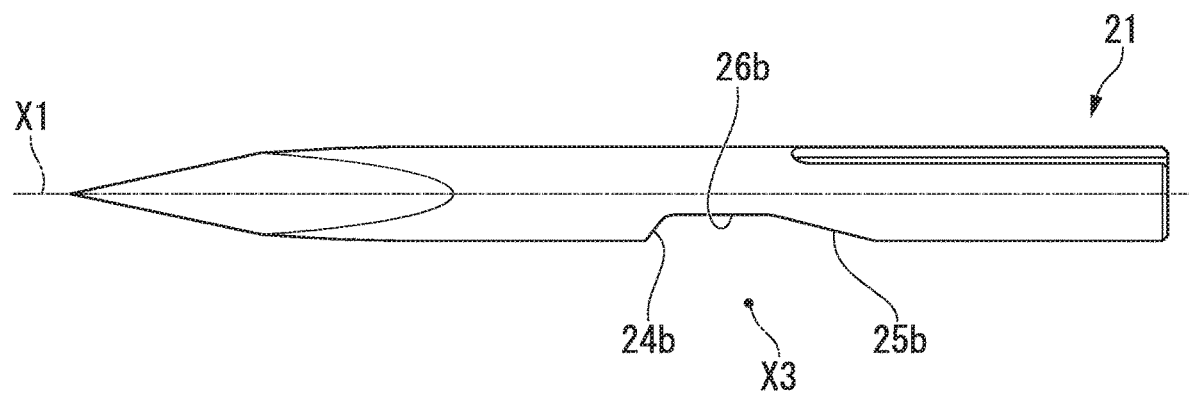
FIG. 5 is a view of the first member viewed from another different direction.

Similarly, the second end surface 24b, the second edge surface 26b, and the second blade surface 25b positioned on the other side with respect to the axis X1 also have a common parallel axis X3 extending in a direction perpendicular to the axis X1 as illustrated in FIG. 5. Therefore, it is possible to form the side hole 23 having the six surfaces and the first protruding portion 27 in the first member 21 through only two processes by forming the first end surface 24a, the first edge surface 26a, and the first blade surface 25a using a laser, a cutter, or the like extending parallel to the parallel axis X2 and forming the second end surface 24b, second edge surface 26b, and the second blade surface 25b using a laser, a cutter, or the like extending parallel to the parallel axis X3. In this manner, while the first member 21 has six surfaces that appear to be a complex shape on the peripheral edge of the side hole 23, it is actually configured to have extremely excellent processability.

Figure 6:
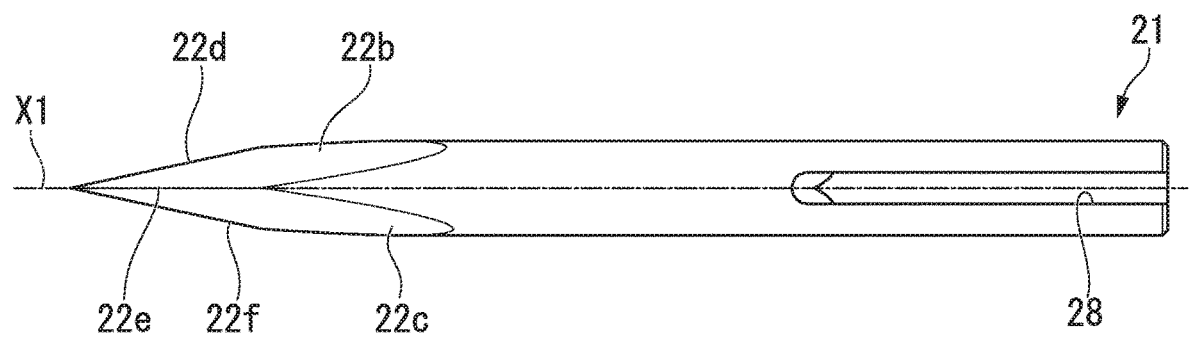
FIG. 6 is a view of the first member viewed from yet another different direction.

FIG. 6 is a view of the first member 21 viewed from the side opposite to the opening of the side hole 23. A groove 28 with which the second member 36 is engaged is formed in the region on the proximal end side with respect to the side hole 23.

Also, as illustrated in FIGS. 3 and 6, the aforementioned piercing portion 22 has three inclined surfaces 22a, 22b, and 22c which are inclined with respect to the axis X1. Ridgelines 22d, 22e, and 22f positioned between adjacent inclined surfaces are positioned at different phases from the first protruding portion 27 in a direction around the axis X1.

Figure 7:
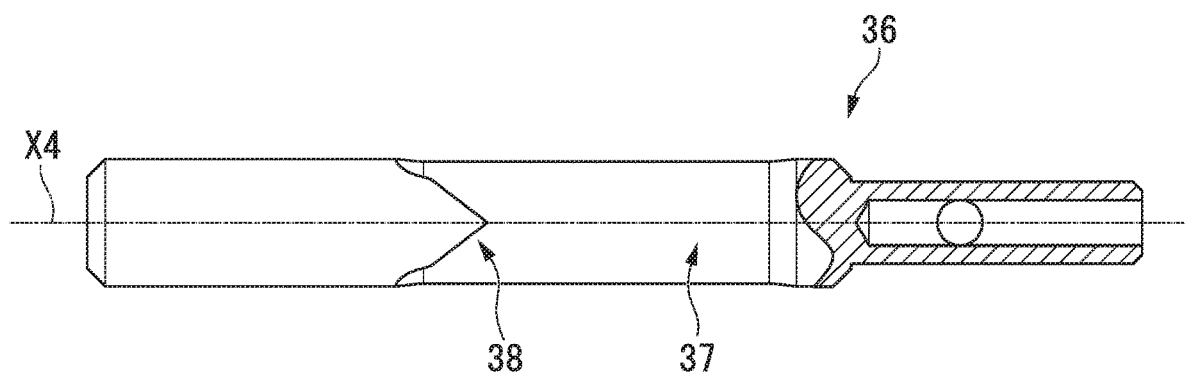
FIG. 7 is a view illustrating a second member of the tissue collecting instrument.

FIG. 7 is a view illustrating the second member 36. The second member 36 is formed by hollowing out a part of a substantially columnar member, and as illustrated in FIG. 2, the hollowed-out portion is an accommodating portion 37 for accommodating tissue. The second member 36 has a second protruding portion 38 protruding toward the proximal end side with respect to the tip of the accommodating portion 37. In the second member 36, the dimension of the region on the distal side with respect to the accommodating portion 37 of substantially a columnar shape in a direction of an axis X4 is longer than the maximum dimension of the side hole 23 in a direction of the axis X1.

As illustrated in FIG. 2, a protrusion 39 is formed on the outer circumferential surface of the second member 36. The second member 36 is inserted into the first member 21 from the distal side so that the protrusion 39 enters the groove 28. Since the protrusion 39 and the groove 28 are engaged with each other, the second member 36 is disposed to be movable relative to the first member 21 in the direction of the axis X1 without rotating around the axis X1. In a state in which the second member 36 is inserted into the first member 21, the second protruding portion 38 protrudes in a direction opposite to the first protruding portion 27.

In a state in which the protrusion 39 and the groove 28 are engaged with each other, the first protruding portion 27 of the first member 21 and the second protruding portion 38 of the second member 36 are positioned at substantially the same phase in a direction around the axis X1 and face each other. The side hole 23, the internal space S, and the accommodating portion 37 communicate in a state in which the first protruding portion 27 and the second protruding portion 38 are spaced apart and facing each other. When the second member 36 is moved back relative to the first member 21 by a predetermined length or more in a state in which the side hole 23 and the internal space S communicate with each other, the side hole 23 is shielded by the outer circumferential surface of the region on the distal side of the second member 36 and the internal space S can be closed.

The first member 21 and the second member 36 are formed of a material having a rigidity of a predetermined value or higher so as to be suitably operated in the tissue of a subject to be collected. For example, metals and resins are suitable and ultrafine grained stainless steels are particularly suitable.

As illustrated in FIG. 1, a main body 51 to which a proximal end portion of the insertion portion 10 is connected, a first slider 52 connected to the first member 21, and a second slider 53 connected to the second member 36 are provided in the manipulator 50. The first slider 52 is connected to the first member 21 via a manipulation coil 41 illustrated in FIG. 2. The first slider 52 is disposed to be slidable relative to the main body 51, and it is possible to make the tissue collecting portion 20 protrude from the insertion portion 10 or accommodate the tissue collecting portion 20 in the insertion portion 10 by sliding the first slider 52 relative to the main body 51.

The second slider 53 is connected to the second member 36 via a manipulation wire 42 inserted through the manipulation coil 41 (see FIG. 2). The second slider 53 is disposed to be slidable relative to the main body 51 and the first slider 52, and it is possible to move the second member 36 forward and backward relative to the first member 21 by sliding the second slider 53 relative to the first slider 52.

The operation of the tissue collecting instrument 1 of the present embodiment configured as above will be described with reference to a case in which a pancreas is taken as an example of subject tissues to be collected (hereinafter, simply referred to as "subject tissue").

First, an operator introduces an endoscope, which is not illustrated, into a body of a patient and moves the distal end portion of the endoscope close to the pancreas. Next, the tissue collecting instrument 1 is inserted into a forceps channel of the endoscope from the distal side thereof in a state in which the tissue collecting portion 20 is accommodated in the insertion portion 10, and the distal portion of the insertion portion 10 is protruded from a distal opening of the forceps channel. The endoscope used may be appropriately selected from a variety of known endoscopes such as optical endoscopes or ultrasonic endoscopes depending on types or positions of subject tissues.

Figure 8:
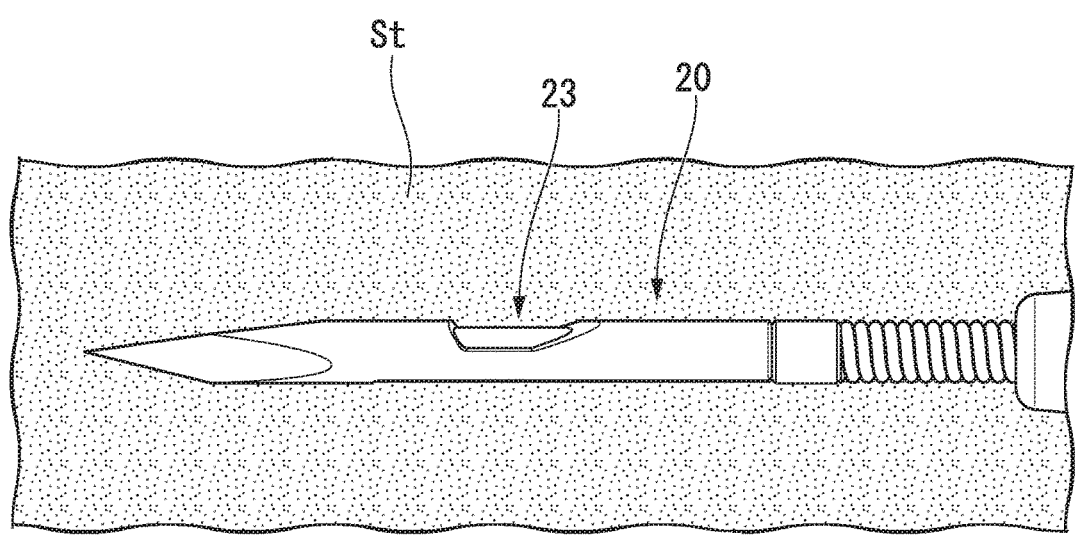
FIG. 8 is a view illustrating a process when the tissue collecting instrument is used.

The operator moves the first slider 52 and the second slider 53 forward relative to the main body 51 so that the tissue collecting portion 20 protrudes from the insertion portion 10 while the pancreas and a site from which a tissue sample is to be collected in the pancreas are observed through endoscope images. At this point, the second slider 53 is moved back by a predetermined amount relative to the first slider 52 in advance to shield the side hole 23 of the first member 21. The operator pierces the pancreas which is the subject tissue with the piercing portion 22 so that the tissue collecting portion 20 enters the subject tissue St until the side hole 23 enters the subject tissue St while the side hole 23 is maintained in a shielded state, as illustrated in FIG. 8.

Subsequently, the operator moves the second slider 53 forward relative to the first slider 52. Thereby, the second member 36 moves forward relative to the first member 21, in the first member 21. As a result, the side hole 23 is opened and communicates with the accommodating portion 37 of the second member 36 provided in the internal space S.

Figure 9:
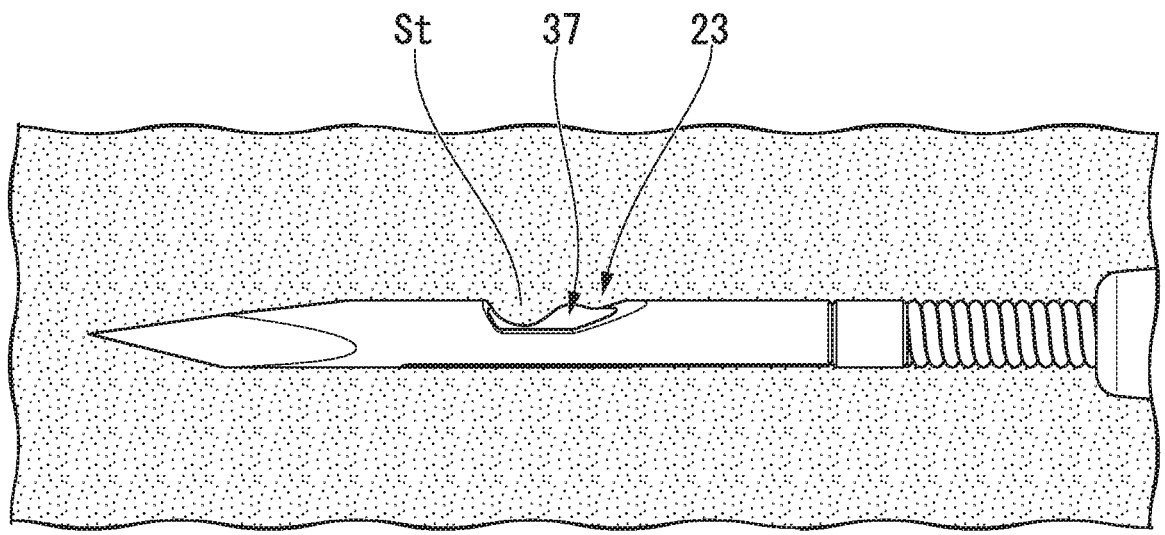
FIG. 9 is a view illustrating a process when the tissue collecting instrument is used.

As illustrated in FIG. 9, since the side hole 23 is opened, some of the subject tissue St enters the accommodating portion 37 in the internal space S through the side hole 23.

Figure 10:
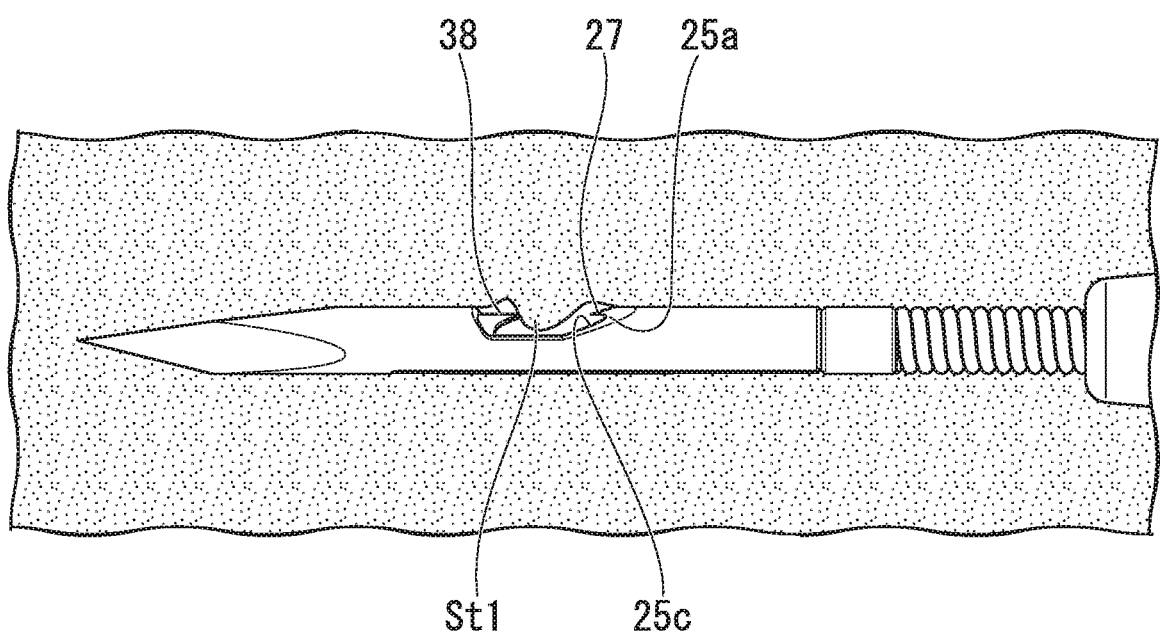
FIG. 10 is a view illustrating a process when the tissue collecting instrument is used.

When the operator moves the second slider 53 back relative to the first slider 52, the second member 36 moves to the proximal end side in the first member 21. As a result, the second protruding portion 38 stabs tissue St1 that has entered the accommodating portion 37 as illustrated in FIG. 10.

Figure 11:
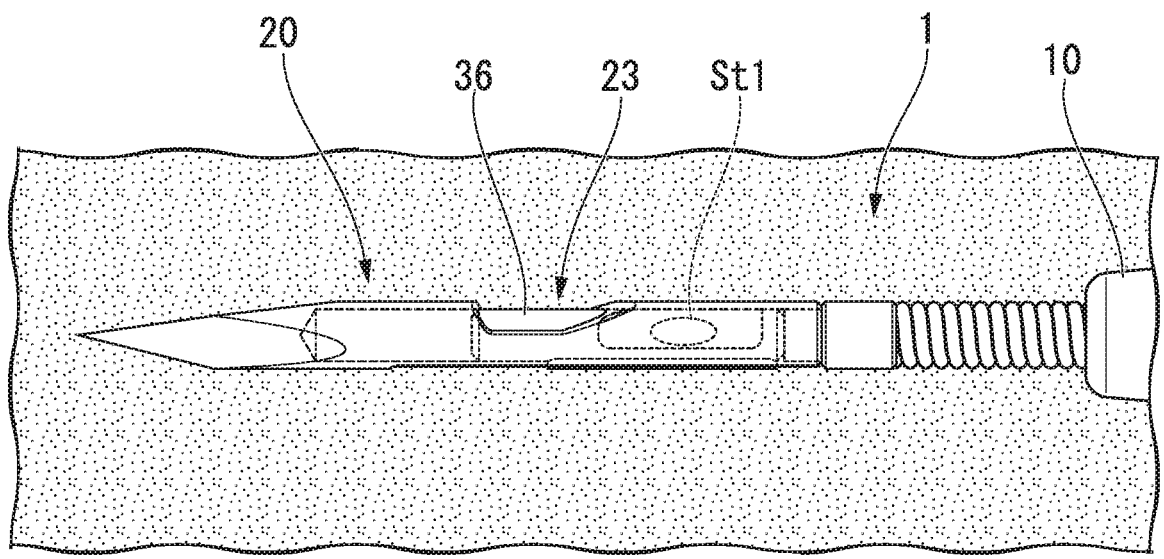
FIG. 11 is a view illustrating a process when the tissue collecting instrument is used.

When the operator further moves the second slider 53 back relative to the first slider 52, the second member 36 that has been driven into the tissue St1 pulls the tissue St1 toward the proximal end side to approach the first protruding portion 27. When the tissue St1 comes into contact with the first protruding portion 27, the edges 25c and 25d continuous with the tip of the first protruding portion 27 are brought into contact with the tissue St1, and the tissue St1 is gradually cut by the first blade surface 25a and the second blade surface 25b. Finally, the tissue St1 is cut off the subject tissue St and is accommodated in the accommodating portion 37 as illustrated in FIG. 11.

The operator moves the tissue collecting portion 20 back and accommodates it in the insertion portion 10 while a state in which the side hole 23 is shielded by the second member 36 is maintained. When the tissue collecting instrument 1 and the endoscope are removed from the body, a sequence of the operation is completed.

As described above, according to the tissue collecting instrument 1 of the present embodiment, in a state in which the side hole 23 of the first member 21 is open to enable some of the subject tissue to enter the internal space S, it is possible for the first protruding portion 27 provided in the first member 21 and the second protruding portion 38 provided in the second member 36 to set in a positional relationship in which the first protruding portion 27 and the second protruding portion 38 face each other in the direction of axis X1 with the side hole 23 interposed therebetween.

Accordingly, the tissue St1 that has entered the internal space S is firmly pierced and hooked by the second protruding portion 38, and can be reliably moved toward the first protruding portion 27 with which the first blade surface 25a and the second blade surface 25b are continuous for cutting the tissue St1. As a result, the tissue St1 is reliably cut and taken by the first blade surface 25a and the second blade surface 25b, and a sufficient volume of tissue sample can be collected without forming negative pressure inside the tissue collecting portion 20 by suction using a syringe or the like.

Also, since the tissue collecting instrument 1 is configured such that the side hole 23 can be shielded by the second member 36, the side hole 23 is shielded before and after collecting the tissue and it is possible to suitably prevent tissue other than the subject tissue, body fluids, or the like from entering the internal space S. As a result, it is not necessary to use a stylet or the like to prevent foreign substances from being introduced as in conventional biopsy devices, and degradation in flexibility of the tissue collecting portion 20 and the manipulation coil 41 is not caused by insertion of a stylet.

In addition, the piercing portion 22 which pierces the tissue has three inclined surfaces and three ridgelines, and all of the three ridgelines 22d, 22e, and 22f are positioned at different phases from the first protruding portion 27 in the direction around the axis X1 of the first member 21. Thereby, the subject tissue St positioned near the side hole 23 is not cut by the ridgelines 22d, 22e, and 22f, and easily enters the internal space S through the side hole 23.

Although an example in which the first member has the piercing portion has been described in the present embodiment, the piercing portion is not essential in the tissue collecting instrument of the present invention.

Figure 12:
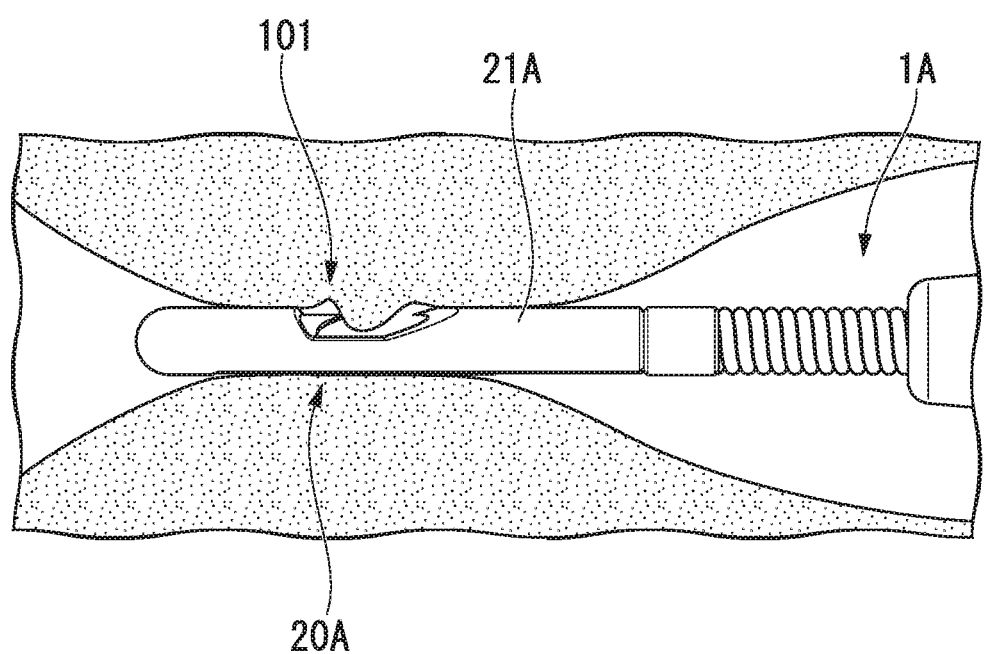
FIG. 12 is a view illustrating a process when a modified example of the tissue collecting instrument is used.

Therefore, a tip of a first member 21A may be formed in a rounded shape such that the tip has a curved surface as in a tissue collecting instrument 1A of the modified example illustrated in FIG. 12. Even with such a shape, as illustrated in FIG. 12, some tissue of a stenosis portion 101 can be reliably collected in a sufficient amount by having a tissue collecting portion 20A enter the stenosis portion 101 such as a bile duct, a pancreatic duct, or the like.

A second embodiment of the present invention will be described with reference to FIGS. 13 and 14. A tissue collecting instrument 61 of the present embodiment is different from the tissue collecting instrument 1 of the first embodiment in shapes of the first member and second member. In the following description, components the same as those already described are denoted by the same reference signs and duplicated descriptions thereof will be omitted.

Figure 13:
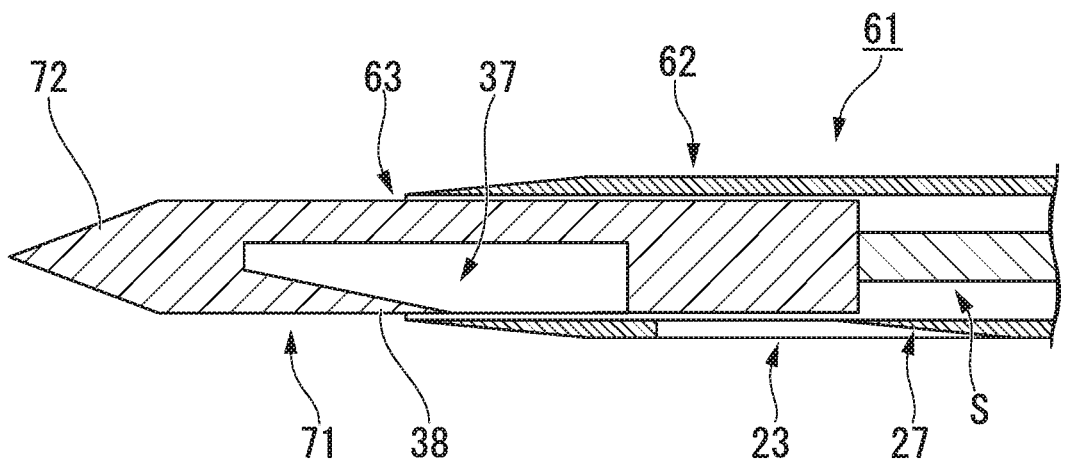
FIG. 13 is an enlarged cross-sectional view schematically illustrating a distal portion of a tissue collecting instrument according to a second embodiment of the present invention.
Figure 14:
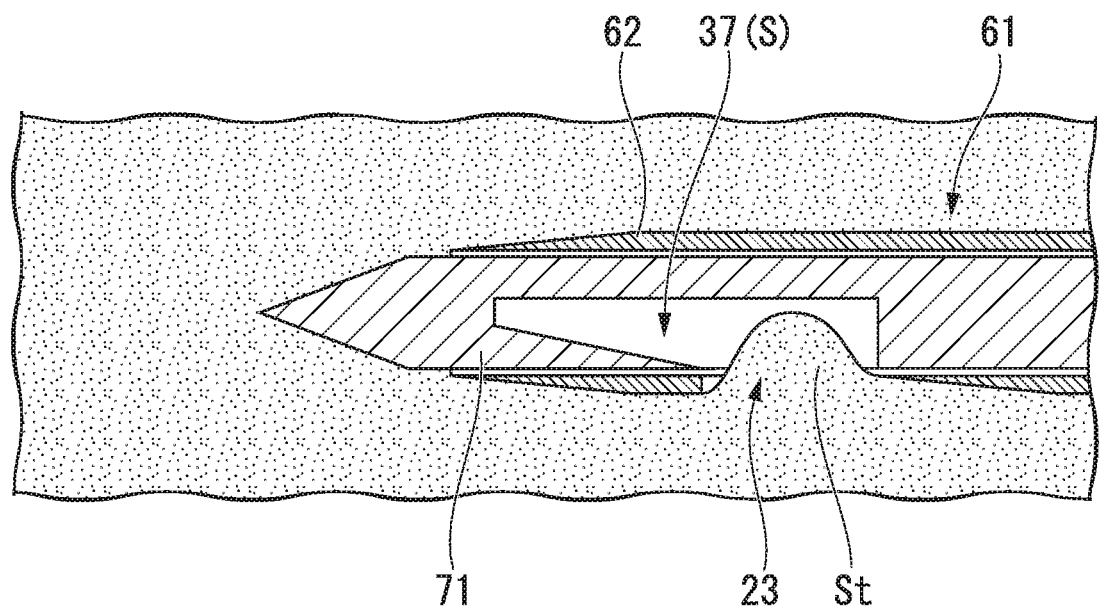
FIG. 14 is a view illustrating a process when the tissue collecting instrument is used.

FIG. 13 is an enlarged cross-sectional view schematically illustrating a distal portion of the tissue collecting instrument 61. A first member 62 is formed in a tubular shape having an opening 63 at its distal end. A piercing portion 72 is formed at the distal end portion of a second member 71. The outer circumferential surface of the distal portion of the first member 62 is formed to gradually decrease in outer diameter approaching the opening 63 so that a large step difference with respect to the outer surface of the piercing portion 72 is not formed when the piercing portion 72 protrudes from the opening 63.

The operation of the tissue collecting instrument 61 configured as above will be described.

When subject tissue is pierced by the tissue collecting instrument 61 the second member 71 is moved forward relative to the first member 62 to cause the piercing portion 72 to protrude from the opening 63 and shield a side hole 23 as illustrated in FIG. 13. When the second member 71 is moved back in the subject tissue, the side hole 23 is opened to communicate with an internal space S and some of subject tissue St enters the internal space S through the side hole 23 as illustrated in FIG. 14. Subsequent procedures of collecting tissue is generally the same as the first embodiment.

In the tissue collecting instrument 61 of the present embodiment as well, as in the tissue collecting instrument 1 of the first embodiment, a sufficient volume of tissue slice can be reliably collected.

Although the embodiments of the present invention have been described above, the technical scope of the present invention is not limited to the above embodiments, and various modifications can be added to the scope of the present invention without departing from the spirit of the present invention.

For example, a known dimple structure may be provided on the surface of the first member or the second member to facilitate visual recognition of the tissue collecting portion with an ultrasonic endoscope.

Also, the disposition of the first protruding portion and the second protruding portion may be reversed. That is, the first protruding portion may be provided on the distal side of the tissue collecting instrument, and the second protruding portion may be provided on the proximal side of the tissue collecting instrument. In this case, the tissue is collected by moving the second member forward relative to the first member.

Also, there may be a configuration allowing more reliable pulling of the tissue toward the first protruding portion by providing a plurality of protruding portions in the second protruding portion, or the like.

In addition, the tissue collecting portion may be configured such that the tissue is directly accommodated in the internal space of the first member without an accommodating portion provided in the second member.

In addition, the cutaway shape of the first member formed on the peripheral edge of the side hole is not limited to that having the above-described six surfaces, and may be appropriately modified. For example, it may be configured to have four surfaces by making the first edge surface and the first end surface into one continuous surface.

As another example, the second end surface, the second edge surface, and the second blade surface may be formed not to have a common parallel axis while the first end surface, the first edge surface, and the first blade surface may be formed to have a common parallel axis. In this case, while excellence in processability is slightly degraded, it is possible to have a configuration such that the same effect of tissue collecting performance as that of the above-described embodiments is achieved.

Subject tissues of the tissue collecting instrument of the present invention are not limited to the above-described pancreas or bile duct. Therefore, any tissue that can be approached by various known endoscopes can be a subject.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A tissue collecting instrument which cuts and collects tissue, comprising:
   a first member formed in a tubular shape and including an internal space and a side hole communicating with the internal space;
   a second member inserted into the internal space and configured to be movable relative to the first member;
   a first protruding portion provided on the first member and configured to protrude toward the inside of the side hole;
   a second protruding portion provided on the second member and configured to protrude in a direction opposite to the first protruding portion;
   wherein the tissue is able to enter the internal space through the side hole when the first member and the second member are in a positional relationship in which the first protruding portion and the second protruding portion are spaced apart and facing each other;

wherein a cutaway surface forming a peripheral edge of the side hole comprises:

a first blade surface and a second blade surface which are configured to form the first protruding portion, wherein the first protruding portion comes to a first point along a centerline of the first member, and wherein the second protruding portion comes to a second point along the centerline of the first member;

a first edge surface and a second edge surface which are configured to form an edge portion in a radial direction of the side hole; and a first end surface and a second end surface which are configured to form an edge portion opposite to the first protruding portion in the side hole;

wherein the first blade surface, the first edge surface, and the first end surface are formed to have a common parallel axis.

2. The tissue collecting instrument according to claim 1, wherein the second blade surface, the second edge surface, and the second end surface are formed to have another common parallel axis.

\* \* \* \* \*